United States Patent [19]

Cepeda et al.

[11] Patent Number: 5,929,121
[45] Date of Patent: *Jul. 27, 1999

[54] PROTECTION OF TREES

[75] Inventors: Jorge Cepeda; Juan Bocanegra, both of Miami, Fla.

[73] Assignee: Rhone-Poulenc Agro, Lyon, Cedex, France

[*] Notice: This patent issued on a continued prosecution application filed under 37 CFR 1.53(d), and is subject to the twenty year patent term provisions of 35 U.S.C. 154(a)(2).

[21] Appl. No.: 08/764,928

[22] Filed: Dec. 13, 1996

[51] Int. Cl.[6] .......................... A01N 33/24; A01N 43/08; A01N 43/40; A01N 57/00
[52] U.S. Cl. ............................ 514/640; 514/92; 514/144; 514/341; 514/357; 514/469; 514/470; 514/626
[58] Field of Search ............................ 514/640, 92, 144, 514/341, 357, 469, 470, 626

[56] References Cited

U.S. PATENT DOCUMENTS

| | | | |
|---|---|---|---|
| 4,918,085 | 4/1990 | D'Silva et al. | 514/407 |
| 5,104,994 | 4/1992 | Roberts et al. | 548/376 |
| 5,177,100 | 1/1993 | Roberts et al. | 514/407 |
| 5,232,940 | 8/1993 | Hatton et al. | 514/407 |
| 5,236,938 | 8/1993 | Huang et al. | 514/341 |

FOREIGN PATENT DOCUMENTS

| | | |
|---|---|---|
| 2147546 | 10/1995 | Canada . |
| 19511269 | 10/1995 | Germany . |
| WO 87/03781 | 7/1987 | WIPO . |
| WO 93/06089 | 4/1993 | WIPO . |
| WO 94/21606 | 9/1994 | WIPO . |

OTHER PUBLICATIONS

Tavares et al, C.A., vol. 95 (1981) 95:182,228X.
Carvalho et al, C.A., vol. 97(1982) 97:105,549S.
Worthing et al, The Pesticide Manual, 9th ed. (1991) pp. 16 & 17.

*Primary Examiner*—Allen J. Robinson
*Attorney, Agent, or Firm*—Morgan & Finnegan, LLP

[57] ABSTRACT

A method for the protection of trees of the families Musaceae or Plantanginaceae from destructive pests whereby the trees to be protected share a common root system.

25 Claims, No Drawings

PROTECTION OF TREES

This invention relates to a new method of protecting trees of the families Musaceae (banana) and Plantanginaceae (plantains) from harmful or destructive pests.

Global regulatory requirements are becoming more and more demanding with respect to the use of pesticides particularly with respect to unmanaged or unnecessary pesticide residues. Thus there exist mutually contradictory requirements of farmers in that the need to control destructive pests very thoroughly demands that more pesticides be used, while increasing pressures from regulatory agencies demand that less pesticides be used. These regulatory demands are aimed to protect the safety and health of agricultural workers and the general public. It also well known that the general public would like less chemical residues on fruits and vegetables.

A particular consequence of this situation is that there is an increasing need to have more efficient methods of protection of banana trees and plantain trees. It is well known that such fruit-producing trees attract a large number of pests, particularly destructive insects and nematodes.

A common technique for cultivating banana trees or plantain trees is by growing them on large blocks or plantations. The trees are disposed as mother plants having a series (for example 1 to 5, generally 1 to 3) of followers or peeps, that is daughter plants, growing from the corm (that is, the base of the pseudotrunk) of the mother plant. In this respect the mother and daughter plants share a common root system. At an appropriate time before the harvest of the fruit of the mother plants or trees, all the daughter plants are removed except one per mother plant which are deemed by the grower to have the best chances of survival. Such a practice allows the next generation of banana or plantain plants to be readily produced. The removal of the daughter plants is possible after the harvest of the mother plants, but it is agronomically preferred to remove them beforehand.

The fruits of the banana trees are harvested by cutting off the bunches of fruit. Afterwards, the mother trees are cut to remove the canopies. The pseudotrunks which are left are generally in a height range from 0.5 meters to 2.5 meters. Such a practice facilitates the growth of the daughter plants. The mother pseudotrunk is then left to decay or is cut down in stages until only a daughter pseudotrunk remains.

Therefore there exists a need to provide an improved method of protection for daughter banana trees and plantain trees from pests which is efficient against destructive pests, especially insects and nematodes and whereby the interval from the treatment of said trees by a pesticide to harvest is as long as possible and whereby the worker exposure is at a minimal level. It has now been found that these needs may be met in whole or in part by means of the instant invention.

According to the invention, a pesticide is found to be most advantageously applied onto or into the pseudotrunk of the cut mother tree in order to protect the daughter tree. In another embodiment, after the initial removal of the canopy of the mother tree the daughter plants may be allowed to develop and the mother pseudotrunk gradually reduced in size by subsequent cuts. A pesticide may be applied onto or into the mother pseudotrunk at any point during this time including when the mother pseudotrunk has been effectively removed. However, it is most advantageous to apply the pesticide early in the development of the daughter plant in order to maximise the treatment-harvest time interval.

The instant invention is related to a method for the protection of two or more trees of the families Musaceae or Plantanginaceae from destructive pests wherein the trees to be protected share a common root system which method comprises:

(a) cutting one of the trees sharing the said root system to remove its fruit and (b) then introducing a pesticide into the said cut tree.

The pesticide may be introduced into any portion of the said cut tree. According to a feature of the invention, the pesticide is introduced into the cut of the tree. According to another feature of the invention, the tree is cut to remove its canopy after the removal of its fruit and before introducing pesticide. The pesticide is, in a preferred feature of the invention, then introduced into the cut of the tree formed by the removal of the canopy.

The pesticide is generally an insecticide, nematicide, fungicide or plant growth regulator, preferably an insecticide or nematicide. The pesticide is generally translocatable and more preferably water soluble at ambient temperature, the water solubility being generally higher than 0.5 g/l, preferably higher than 2 g/l at ambient temperature. The pesticide can be provided in a formulation that is generally translocatable and more preferably water soluble at ambient temperature.

Those species of banana or plantain trees to be preferably protected according to the present invention are *Musa textilis, Musa sapientum,* or *Musa paradisica.*

The pesticide is generally introduced into the tree from zero to about thirty days after one of the trees is cut, preferably from about one to about seven days and even more preferably from about two to about three days.

A preferred group of insecticides or nematicides according to the invention are carbamates. Carbamates are a well-known group of pesticides: those skilled in the art will recognise these in *The Pesticide Manual* 10th ed., edited by C. Tomlin, British Crop Protection Council, United Kingdom, 1994. A preferred group of carbamates are N-methyl carbamates, that is those substances that possess the substituent —OC(O)NHMe. A particularly preferred carbamate that can be used according the instant invention is 2-methyl-2-(methylthio)propionaldehyde O-methylcarbamoyloxime (aldicarb). Other carbamates that can be used according to the invention are 2,3-dihydro-2,2-dimethylbenzofuran-7-yl methylcarbamate (carbofuran) and N,N-dimethyl-2-methylcarbamoyloxyimino-2-(methylthio) acetamide (oxamyl). A carbamate can be used alone or in combination with other pesticides.

Other insecticides or nematicides that can be used according to the instant invention either alone or in combination with other pesticides include:

nitromethylenes or nitroimines including 1-(6-chloro-3-pyridylmethyl)-N-nitroimidazolidin-2-ylideneamine (imidacloprid);

cyanoimines including (E)-$N^1$-[(6-chloro-3-pyridyl)methyl]-$N^2$-cyano-$N^1$-methylacetamidine (acetamiprid); and organophosphates including S,S-di-sec-butyl O-ethyl phosphorodithioate (cadusafos);

(RS)-S-sec-butyl O-ethyl 2-oxo-1,3-thiazolidin-3-ylphosphonothioate (fosthiazate); and O-ethyl S,S-dipropyl phosphorodithioate (ethoprophos).

Other insecticides or nematacides that can be used according to the instant invention either alone or in combination with other pesticides include compounds of formula (I):

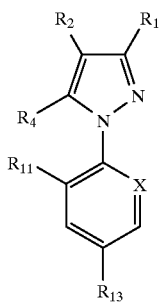

(I)

in which:

R$_1$ is —CN or methyl;
R$_2$ is —S(O)$_n$R$_3$;
R$_3$ is alkyl or haloalkyl;
R$_4$ represents a hydrogen or halogen atom or a member of a group consisting of —NR$_5$R$_6$, —S(O)$_m$R$_7$, —C(O)O—R$_7$, alkyl, haloalkyl, —OR$_8$ and —N=C(R$_9$)(R$_{10}$);
R$_5$ and R$_6$ independently represent the hydrogen atom or an alkyl, haloalkyl, —C(O)alkyl, alkoxycarbonyl or —S(O)$_r$CF$_3$ radical; or R$_5$ and R$_6$ can together form a divalent alkylene radical which can be interrupted by one or two divalent heteroatoms, such as oxygen or sulfur;
R$_7$ represents an alkyl or haloalkyl radical;
R$_8$ represents an alkyl or haloalkyl radical or a hydrogen atom;
R$_9$ represents an alkyl radical or hydrogen atom;
R$_{10}$ represents a phenyl or heteroaryl group which is unsubstituted or substituted by one or more halogen atoms or a member of the group consisting of —OH, —O-alkyl, —S-alkyl, cyano, and alkyl;
X represents a trivalent nitrogen atom or a —C—R$_{12}$ radical, the other three valences of the carbon atom forming part of the aromatic ring;
R$_{11}$ and R$_{12}$ represent, independently of one another, a hydrogen or halogen atom;
R$_{13}$ represents a halogen atom or a haloalkyl, haloalkoxy, —S(O)$_q$CF$_3$ or SF$_5$ group;
m, n, q, and r represent, independently of one another, an integer equal to 0, 1, or 2;
provided that, when R$_1$ is methyl, then R$_3$ is haloalkyl, R$_4$ is —NH$_2$, R$_{11}$ is —Cl, R$_{13}$ is CF$_3$ and X is N.

By the term "alkyl" is meant carbon chains of from one to six carbon atom that are either linear or branched chains. By the term "divalent alkylene" is meant a carbon chain that attaches at two points to the nitrogen atom of the radical R$_4$.

A preferred group of compounds of formula (I) is one in which:

R$_1$ is CN;
R$_3$ is a haloalkyl radical;
R$_4$ is NH$_2$;
X is C—R$_{12}$;
R$_{11}$ and R$_{12}$ represent, independently of one another, a halogen atom; and
R$_{13}$ is a haloalkyl radical.

A most highly preferred compound of formula (I) is 5-amino-1-(2,6-dichloro 4-trifluoromethyl phenyl) 4trifluoromethylsulfinyl-3-cyanopyrazole.

Compounds of formula (I) may be prepared according to known processes, for example as described in International Patent Publications No. WO 87/3781, 93/6089, and 94/21606 as well as in European Patent Applications 295117, 403300, 385809 or 679650, German Patent Publication 19511269 and U.S. Pat. Nos. 5,232,940 and 5,236,938 or other process according to the knowledge of a man skilled in the art of chemical synthesis.

Pests that may be controlled according to the instant invention include *Cosmopolites sordidus* (banana weevil), *Radopholus similis* (burrowing nematode), *Helicotylenchus multicinctus* (Spiral nematode), *Meloidogyne incognita* (Rootknot nematode) and pests of the families Heteroderidae and Thripidae.

Fungicides that may be used according to the instant invention include:

methyl 1-(butylcarbamoyl)benzimidazol-2-ylcarbamate (benomyl);

triazoles including (±)-1-[2-(2,4-dichlorophenyl)-4-propyl-1,3-dioxolan-2-ylmethyl]-1H-1,2,4-triazole (propiconazole); and 1-[(2RS,4RS:2RS,4SR)-4-bromo-2-(2,4dichlorophenyl) tetrahydrofurfuryl]-1H-1,2,4-triazole (bromuconazole).

Plant growth regulators that may be used according to the instant invention include:

a gibberellin such as gibberellic acid or
2-chloroethylphosphonic acid (ethephon).

The amount of pesticide which is used is an effective and agronomically acceptable amount per tree. In the case of 2-methyl-2-(methylthio)propionaldehyde O-methyl-carbamoyloxime, quantities of from 0.01 to 5 g per tree may be appropriate, preferably from 0.3 to 0.9 g per tree.

The introduction of the pesticide in the pseudotrunk of the tree is made by insertion of a composition, which can be of liquid or solid formulation, preferably solid, in order to reduce worker exposure, especially with compounds having relatively high acute toxicity. A solid formulation is preferred for 2-methyl-2-(methylthio)propionaldehyde O-methylcarbamoyloxime.

Formulations are chosen so as to speed the transmission of the active ingredient into an aqueous phase such as the vascular tissue normally present in plants or trees. Formulations are also chosen in order to minimise the exposure of agricultural workers to the pesticide.

Still more preferable are those substantially dustless formulations, for example those whose particle size is greater than 0.1 mm, preferably from 0.4 to 0.8 mm. Acceptable formulations may be made by mixing the active ingredient with a polymer, especially a water soluble polymer. Gels may also be used.

The introduction of the pesticide into the pseudotrunk of the mother tree may be made by any suitable means. One possibility is the injection of the pesticide into the pseudotrunk. Another possibility is to make or drill holes in the tree and to put therein the formulation and then to plug or stop the holes. The holes may be made on the lateral part of the pseudotrunk, but it is preferred to make the insertion where the pseudotrunk was cut to remove the canopy.

Another method of introduction of the pesticide is to cut a wedge out of the pseudotrunk, add the pesticidal formulation and replace the wedge back into the space from which it came. An especially preferred embodiment of this insertion is to cut the wedge out from the surface of the cut made by removing the canopy.

Another embodiment is the insertion into the pseudotrunk of a water-soluble capsule containing a dose of the desired pesticide.

The following non-limiting-example is given to illustrate the invention.

EXAMPLE

Banana trees are grown in a plantation. The trees are disposed as mother plants having a series (1 to 5) of daughter plants growing from the corm. Just before harvesting the mother plants, the daughter plants are removed except one daughter plant per mother plant.

The fruit of the banana trees are harvested by cutting the sets of fruits. Within one week after this harvest, the pseudotrunks of these plants are cut to remove the canopies. After two days a wedge is cut from the surface resulting from the removal of the canopy of each pseudotrunk of each mother tree. A dose of 0.5 g per tree of 2-methyl-2-(methylthio)propionaldehyde O-methylcarbamoyloxime in the form of a 15% w/w granular formulation is placed in the empty concave space from which each wedge was removed and the wedges are replaced.

The daughter plants are protected against both nematodes and weevils up to harvest time of the daughter trees which is 35 weeks later thus to provide economically acceptable fruit The risk of worker exposure is greatly reduced.

We claim:

1. A method for the enhanced protection of trees of the families Musaceae or Plantanginaceae from destructive pests, wherein the trees to be protected share a common root system, which method comprises the combination of steps of:

(a) cutting at least one of the trees sharing the root system to remove its fruit, and (b) then introducing a pesticide into at least one of the cut trees, wherein the pesticide comprises an insecticide or a nematicide and is introduced in an effective amount per tree.

2. A method according to claim 1, wherein after cutting one of the trees to remove fruit in step (a) but before introducing the pesticide in step (b), the cut tree is further cut to remove its canopy.

3. A method according to claim 1, wherein the pesticide is introduced into the cut of the tree formed by removal of the fruit.

4. A method according to claim 2, wherein the pesticide is introduced into the cut of the tree formed by the removal of the canopy.

5. A method according to claim 1, wherein the pesticide is introduced into a lateral portion of the tree.

6. A method according to claim 1, wherein the pesticide is introduced from zero to about thirty days after the tree is cut.

7. A method according to claim 1 wherein the pesticide is generally translocatable at ambient temperature.

8. A method according to claim 1 wherein the pesticide is provided in a formulation which is water soluble at ambient temperature.

9. A method according to claim 1 wherein the trees are either *Musa textilis, Musa sapientum,* or *Musa paradisica.*

10. A method according to claim 1, wherein the insecticide or nematicide is a carbamate.

11. A method according to claim 1, wherein the insecticide or nematicide is 2-methyl-2-(methylthio) propionaldehyde O-methylcarbamoyloxime or 2,3-dihydro-2,2-dimethylbenzofuran-7-yl methylcarbamate.

12. A method according to claim 11 wherein the amount of 2-methyl-2-(methylthio) propionaldehyde O-methylcarbamoyloxime or 2,3-dihydro-2,2-dimethylbenzofuran-7yl methylcarbamate used per tree is from 0.01 g and 5 g per tree.

13. A method according to claim 1 wherein the insecticide or nematicide is:

1-(6-chloro-3-pyridylmethyl)-N-nitroimidazolidin-2-ylideneamine (imidacloprid);

(E)-$N^1$-[(6-chloro-3-pyridyl)methyl]-$N^2$-cyano-$N^1$-methylacetamidine (acetamiprid);

N,N-dimethyl-2-methylcarbamoyloxyimino-2-(methylthio)acetamide (oxamyl);

S,S-di-sec-butyl O-ethyl phosphorodithioate (cadusafos);

(RS)-S-sec-butyl O-ethyl 2-oxo-1,3-thiazolidin-3-ylphosphonothioate (fosthiazate); or O-ethyl S,S-dipropyl phosphorodithioate (ethoprophos).

14. A method according to claim 1 wherein the pesticide used is in a solid or liquid formulation.

15. A method according to claim 14 wherein the formulation is substantially dustless.

16. A method according to claim 14 wherein the formulation has a particle size greater than 0.1 mm.

17. A method according to claim 14, wherein said pesticide is a solid formulation.

18. A method according to claim 1, wherein said pesticide is 2-methyl-2-(methylthio) propionaldehyde O-methylcarbamoyle oxime.

19. A method according to claim 12, wherein said amount is from 0.3 g to 0.9 g per tree.

20. A method according to claim 14, wherein said formulation is a solid formulation.

21. A method according to claim 16, wherein said particle size is from 0.4 to 0.8 mm.

22. A method according to claim 10, wherein said carbamate is an N-methyl carbamate.

23. A method according to claim 1, wherein the pesticide comprises a nitromethylene or nitroimine pesticide.

24. A method according to claim 1, wherein the pesticide comprises a cyanoimine pesticide.

25. A method according to claim 1, wherein the pesticide comprises an organophosphate pesticide.

* * * * *